United States Patent [19]

Daneshtalab et al.

[11] Patent Number: 5,051,515
[45] Date of Patent: Sep. 24, 1991

[54] NOVEL GENERATION OF HETEROARYL THIO, SULFOXY, OR SULFONYL ALKYL AZOLES

[75] Inventors: Mohsen Daneshtalab, Edmonton; Ronald G. Micetich, Sherwood Park; Dai Q. Nguyen, Edmonton; Chan M. Ha, Edmonton; Hiep T. Luu, Edmonton, all of Canada

[73] Assignee: SynPhar Laboratories Incorporated, Alberta, Canada

[21] Appl. No.: 329,040

[22] Filed: Mar. 27, 1989

[30] Foreign Application Priority Data

Mar. 26, 1988 [GB] United Kingdom ............... 8807275

[51] Int. Cl.$^5$ ........................................... C07D 285/12
[52] U.S. Cl. .................................. 548/136; 548/156; 548/215; 548/240; 548/250; 548/335
[58] Field of Search ............... 548/237, 238, 136, 156, 548/240, 250, 215, 335; 424/273

[56] References Cited

U.S. PATENT DOCUMENTS 4,735,955  4/1988  Tomiyamo et al. ............... 548/136

Primary Examiner—Jose G. Dees
Assistant Examiner—Deborah D. Carr
Attorney, Agent, or Firm—Armstrong, Nikaido, Marmelstein, Kubovcik & Murray

[57] ABSTRACT

There are provided compounds having the general formulae

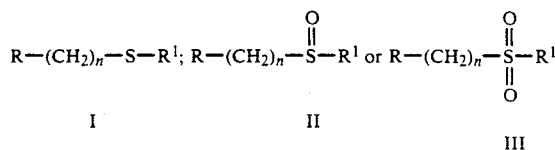

wherein
R is a non-fused azole moiety;
n is 5, 6, 7 or 8; and
R$^1$ is a substituted, fused or non-fused azole moiety.

These compounds have been demonstrated as having antipicornavirus activity.

16 Claims, No Drawings

NOVEL GENERATION OF HETEROARYL THIO, SULFOXY, OR SULFONYL ALKYL AZOLES

FIELD OF THE INVENTION

The present invention relates to novel heteroaryl thio, sulfoxy or sulfonyl alkyl azoles. The invention further relates to processes for the preparation of said compounds and to their utility as antiviral agents.

BACKGROUND OF THE INVENTION

The activity of the class of arildone type compounds as antirhinovirus agents has been well documented and disclosed, for example in U.S. Pat. No. 4,171,365 and European Patent Applications 0 111 345 and 0 137 242, respectively.

SUMMARY OF THE INVENTION

In accordance with the present invention there are provided compounds having the general formulae:

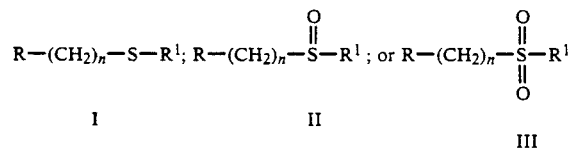

wherein
R is preferably selected from the group comprising 3-methylisoxazol-5-yl; 3,5-dimethylpyrazol-1-yl; 4-methylthiazol-2-yl; 4-methylisothiazol-5-yl; or 5-isothiazolyl;
n is 6 or 7; and
$R^1$ is preferably selected from the group comprising 1-methyltetrazol-5-yl; 5-methyl-1,3,4-thiadiazol-2-yl; 2-benzoxazolyl; 1-methylimidazol-2-yl; 2-benzimidazoyl; 5-chlorobenzimidazol-2-yl; or 2-benzothiazolyl.

Advantageously, physiologically acceptable compounds of formulae I, II or III possess pharmacological properties exhibiting activity, in particular, against rhinoviruses, and coxsacki virus type B-1.

Thus the compounds of the present invention may be utilized as active compounds in medicaments.

Broadly stated, the invention comprises compounds having the general formulae:

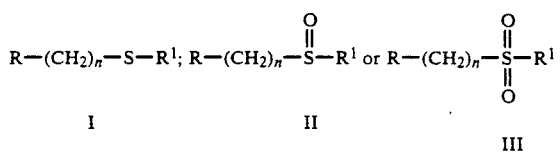

wherein
R is a non-fused azole moiety;
n is 5, 6, 7 or 8; and
$R^1$ is a substituted, fused or non-fused azole moiety.

DESCRIPTION OF THE PREFERRED EMBODIMENT

Compounds of formula I were preferably prepared by refluxing an ω-haloalkyl substituted azole of formula IV

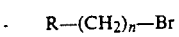   IV with a fused or non-fused mercapto azole in acetone in the presence of potassium carbonate.

Compounds of the formulae II and III were prepared by oxidizing compounds of formula I with either metachloroperbenzoic acid or potassium permanganate in suitable solvents.

The ω-haloalkyl substituted azoles of formula IV were prepared according to the conventional procedure of reacting the lithium or sodium salt of the appropriate azole with a dibromo alkane.

The products obtained by each procedure were purified by recrystallization from a suitable solvent or by elution from a silica gel column using an appropriate solvent system.

All the products of the invention were characterized by their respective nmr, IR spectra and elemental analysis. The relative purity of the compounds was established using HPLC.

More specifically, the ω-haloalkyl substituted azoles having the general formula IV were prepared by reacting a lithium or sodium salt of an azole selected from the group comprising 3,5-dimethylisoxazole; 4-methylthiazole; 4-methylisothiazole; 3,5-dimethylpyrazole or isothiazole with 1,6-dibromohexane in a suitable solvent. The reaction was carried out at −70° for 3–5 h. The yields varied from 40% to 70%.

The substituted fused, or non-fused, mercapto azoles utilized in the synthesis were selected from the group comprising 5-mercapto-1-methyltetrazole; 2-mercapto-5-methyl-1,3,4-thiadiazole; 2-mercaptobenzoxazole; 2-mercapto-1-methylimidazole; 2-mercaptobenzimidazole; 5-chloro-2-mercapto-benzimidazole; or 2-mercaptobenzothiazole.

The related sulfoxy derivatives of formula I, i.e. the compounds of formula II, were prepared by reacting an equimolar amount of the heteroarylthioalkyl azole with metachloroperbenzoic acid (MCPBA) in dichloromethane at room temperature for 0.5–2 h.

Similarly, the related sulfonyl derivatives of formula I, i.e. the compounds of formula III, were prepared by reacting a 1:2 ratio of the heteroarylthio alkyl azole with MCPBA, in dichloromethane at room temperature for 0.5–2 h. Alternatively, the heteroarythioalkyl azole may be reacted with potassium permanganate in acetic acid.

The selected compounds of this invention were tested for anti-rhinoviral activity and other potential pharmacological activity in accordance with known techniques.

More particularly, 2-[7-(benzoxazol-2-yl)thioheptyl]-4-methylthiazole; 5-[7-(1-methylimidazol-2-yl)thioheptyl]-3-methylisoxazole; 5-[7-(1-methylimidazol-2-yl)sulfoxyheptyl]-3-methylisoxazole; 1-[6-(benzoxazol-2-yl)thiohexyl]-3,5-dimethylpyrazole; 5-[7-(benzimidazol-2-yl)thioheptyl]-3-methylisoxazole; 5-[7-(benzimidazol-2-yl)sulfoxyheptyl]-3-methylisoxazole; 5-[7-(benzothiazol-2-yl)thioheptyl]-3-methylisoxazole; and 2-[6-(5-chlorobenzimidazol-2-yl)thiohexyl]-4-methylthiazole demonstrated remarkable activity against HRV-1A and HRV-39 in vitro.

More particularly, 5-[7-(benzimidazol-2-yl)thioheptyl]-3-methylisoxazole and 2-[6-(5-chlorobenzimidazol-2-yl)thiohexyl]-4-methylthiazole were tested against 20 serotypes of rhinoviruses (namely, HRV's 1A, 1B, 2, 4, 15, 17, 23, 29, 30, 31, 32, 36, 39, 44, 49, 53, 56, 63, 86, and 88).

These compounds exhibited MIC-50's which varied from 1 μg/ml to 25 μg/ml.

Compound 2-[6-(5-chlorobenzimidazol-2-yl)thiohexyl]-4-methylthiazole exhibited very strong inhibitory activity against coxsacki virus type B1.

EXAMPLE 1

5-[7-(1-methyltetrazol-5-yl)thioheptyl]-3-methyl isoxazole (1)

R = 3-methylisoxazol-5-yl
n = 7
$R^1$ = 1-methyltetrazol-5-yl.

7-(3-methylisoxazole-5-yl)heptylbromide (520 mg, 0.002 mol) was added to a mixture of 1-methyltetrazole thiol (232 mg, 0.002 mol) and potassium carbonate (276 mg, 0.002 mol) in anhydrous acetone (20 ml) while stirring. The mixture was heated under reflux for 3 hours. After cooling, the mixture was filtered and the filtrate was concentrated under reduced pressure. The residual oil as dissolved in dichloromethane (50 ml), washed with water (50 ml×2), with 5% aqueous solution of potassium hydroxide (10 ml) and again with water (50 ml×2). The organic layer was dried over sodium sulfate. Removal of the solvent gave a yellow oil (600 mg) which was purified by elution from a silica gel column using methanol-dichloromethane (5:95) as an eluant to give 80% (472 mg) of a colorless oil.

NMR (CDCl$_3$, 300 mHz).

1.8–1.3 (m, 10H, (CH$_2$)$_5$); 2.3 (S, 3H, CH$_3$-isoxazol) 2.7 (t, J=8 Hz, 2H, —CH$_2$-isoxazol); 3.35 (t, J-8 Hz, 2H, —CH$_2$—S); 3.9 (S, 9H, CH$_3$—N); 5.8 (S, 1H, H-isoxazol).

Analysis found: C, 52.65; H, 7.22; N, 23.78; S, 10.80; Required: C$_{13}$H$_{21}$N$_5$OS = 295.403; C, 52.86; H, 7.17; N, 23.71; S, 10.85.

Schematic for Example 1

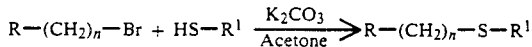

$$R-(CH_2)_n-Br + HS-R^1 \xrightarrow[\text{Acetone}]{K_2CO_3} R-(CH_2)_n-S-R^1$$

By procedures similar to those used in example 1 and starting with the appropriately substituted heterocyclic moiety R and $R^1$, the following compounds were prepared.

EXAMPLE 2

5-[7-(5-methylthiodiazol-2-yl)thioheptyl]-3-methyl isoxazole (2)

R = 3-methylisoxazol-5-yl
n = 7
$R^1$ = 5-methylthiodiazol-2-yl

Colorless prisms, mp 62°–63° C., yield 55%.

NMR (CDCl$_3$, 60 mHz).

1.3–2.00 (m, 10H, (CH$_2$)$_5$); 2.3 (S, 3H, CH$_3$-isoxazole); 2.7 (S, 3H, CH$_3$-thiodiazole); 2.7 (t, J=9 Hz, 2H, —CH$_2$-isoxazole); 3.3 (t, J=9 Hz, 2H, —CH$_2$—S), 5.8 (S, 1H, H-isoxazole) IR (neat).

Analysis found: C, 54.11; H, 6.89; N, 13.37; S, 20.52; Required: C$_{14}$H$_{21}$N$_3$OS$_2$ = 311.46; C, 53.99; H, 6.80; N, 13.49; S, 20.59.

EXAMPLE 3

5-[7-(1-methylimidazol-2-yl) thioheptyl]-3-methyl isoxazole (3)

R = 3-methylisoxazol-5-yl
n = 7
$R^1$ = methylimidazol-2-yl
Yellow oil, yield 58%.

NMR (CDCl$_3$, 200 mHz).

1.5–1.8 (m, 10H, (CH$_2$)$_5$), 2.3 (S, 3H, CH$_3$-isoxazole); 2.7 (t, J=8 Hz, 2H, —CH$_2$-isoxazole); 3.05 (t, J=8 Hz, —CH$_2$—S); 3.6 (S, 3H, CH$_3$—N); 5.8 (S, 1H, H-isoxazole); 6.85 (d, J=2 Hz, 1H, H$_5$-imidazole); 7.05 (d, J=2 Hz, 1H, H$_4$-imidazole).

Analysis found: C, 61.58; H, 7.17; N, 14.15; S, 10.81; Required: C$_{15}$H$_{23}$N$_3$OS = 293.427; C, 61.40; H, 7.9; N, 14.32; S, 10.93.

EXAMPLE 4

5-[7-(benzimidazol-2-yl)thioheptyl]-3-methylisoxazole (4)

R = 3-methylisoxazol-5-yl
n = 7
$R^1$ = benzimidazol-2-yl
Colorless prisms, mp = 84°–85° C., yield 72%.

NMR (CDCl$_3$, 200 mHz).

1.3–1.75 (m, 10H, (CH$_2$)$_5$); 2.3 (S, 3H, CH$_3$-isoxazole); 2.7 (t, J=8 Hz, 2H, —CH$_2$-isoxazole); 3.3 (t, J=8 Hz, 2H, —CH$_2$—S); 5.8 (S, 1H, H-isoxazole); 7.10–7.20 (m, 4H, H-benzimidazole); 7.50 (S, 1H, H—N).

Analysis found: C, 65.80; H, 7.11; N, 12.61; S, 9.65; Required: C$_{18}$H$_{23}$N$_3$OS; C, 65.62; H, 7.04; N, 12.75; S, 9.73.

EXAMPLE 5

5-[7-(5-chlorobenzimidazol-2-yl) thioheptyl]-3-methylisoxazole (5)

R = 3-methylisoxazol-5-yl
n = 7
$R^1$ = 5-chlorobenzimidazol-2-yl
Sticky oil; yield 56%.

NMR (CDCl$_3$, 200 mHz).

1.3–1.75 (m, 10H, (CH$_2$)$_5$); 2.3 (S, 3H, CH$_3$-isoxazole); 2.7 (t, J=8 Hz, 2H, —CH$_2$-isoxazole); 3.3 (t, J=8 Hz, 2H, —CH$_2$—S); 5.8 (S, 1H, H-isoxazole); 7.10 (d, J=2 Hz, 1H, H$_7$-benzimidazole); 7.18 (d, J=2 Hz, 1H, H$_6$-benzimidazole); 7.25 (S, 1H, H$_4$-benzimidazole).

Analysis found: C, 59.55; H, 6.17; N, 11.42; S, 8.65, Cl, 9.63; Required: (C$_{18}$H$_{22}$ClN$_3$OS) = 363.905; C, 59.41; H, 6.09; N, 11.55; S, 8.81; Cl, 9.74.

EXAMPLE 6

5-[7-(benzothiazol-2-yl) thioheptyl]-3-methylisoxazole (6)

R = 3-methylisoxazol-5-yl
n = 7
$R^1$ = benzothiazol-2-yl
Colorless prism, mp = 50°–57° C., yield 70%.

NMR (CDCl$_3$, 200 mHz).

1.3–1.8 (m, 10H, —(CH$_2$)$_5$—); 2.3 (S, 3H, CH$_3$-isoxazole); 2.7 (t, J=8 Hz, 2H, —CH$_2$-isoxazole); 3.3 (t, J=8 Hz, 2H, —CH$_2$—S); 5.8 (S, 1H, H-isoxazole); 7.24–7.88 (m, 4H, H-benzothiazole).

Analysis found: C, 62.51; H, 6.51; N, 8.01; S, 18.39; Required: (C$_{18}$H$_{22}$N$_2$OS$_2$); C, 62.39; H, 6.40; N, 8.08; S, 18.50.

EXAMPLE 7

1-[6-(5-methylthiodiazol-2-yl) thiohexyl]-3,5-dimethylpyrazole (7)

R = 3,5-dimethylpyrazol-1-yl
n = 6

$R^1$ = 5-methylthiodiazol-2-yl

Colorless prism, mp = 40°–42° C., yield 72%.

NMR (CDCl$_3$).

1.3–1.9 (m, 8H, —(CH$_2$)$_4$—); 2.2 (S, 6H, Me$_3$-; Me$_5$-pyrazole); 2.7 (S, 3H, CH$_3$-thiodiazole); 3.3 (t, J = 8 Hz, 2H, CH$_2$—S); 3.95 (t, J = 8 Hz, 2H, —CH$_2$—N); 5.75 (S, 1H, H-pyrazole).

Analysis found: C, 54.31; H, 7.22; N, 17.93; S, 20.53; Required: (C$_{14}$H$_{22}$N$_4$S$_2$); C, 54.16; H, 7.14; N, 18.05; S, 20.65.

EXAMPLE 8

1-[6-(1-methyltetrazol-5-yl) thiohexyl]-3,5-dimethylpyrazole (8)

R = 3,5-dimethylpyrazol-1-yl n = 6

$R^1$ = 1-methyltetrazol-5-yl

Yellow oil, yield 79%.

NMR (CDCl$_3$).

1.3–1.9 (m, 8H, —(CH$_2$)$_4$—); 2.2 (S, 6H, Me$_3$-, Me$_5$-pyrazole); 3.3 (t, J = 8 Hz, 2H, —CH$_2$—S); 3.9 (S, 3H, CH$_3$—N of tetrazole); 3.95 (t, J = 8 Hz, 2H, —CH$_2$—N); 5.75 (S, 1H, H-pyrazole).

Analysis found: C, 53.19; H, 7.61; N, 28.42; S, 10.77; Required: (C$_{13}$H$_{22}$N$_6$S); C, 53.04; H, 7.53; N, 28.53; S, 10.89.

EXAMPLE 9

1-[6-(1-methylimidazol-2-yl) thiohexyl]-3,5-dimethylpyrazole (9)

R = 3,5-dimethylpyrazole-1-yl n = 6

$R^1$ = 1-methylimidazol-2-yl

Colorless oil, yield 63%.

NMR (CDCl$_3$).

1.3–1.9 (m, 8H, —(CH$_2$)$_4$—); 2.2 (S, 6H, Me$_3$-, Me$_5$-pyrazole); 3.05 (t, J = 8 Hz, 2H, CH$_2$—S); 3.6 (S, 3H, CH$_3$—N of imidazole); 3.95 (t, J = 8 Hz, 2H, —CH$_2$—N); 5.75 (S, 1H, H-pyrazole); 6.85 (d, J = 2 Hz, 1H, H$_5$-imidazole); 7.05 (d, J = 2 Hz, 1H, H$_4$-imidazole).

Analysis found: C, 61.83; H, 8.33; N, 18.99; S, 10.85; Required: (C$_{15}$H$_{24}$N$_4$S); C, 61.61; H, 8.27; N, 19.16; S, 10.96.

EXAMPLE 10

1-[6-(benzoxazol-2-yl) thiohexyl]-3,5-dimethylpyrazole (10)

R = 3,5-dimethylpyrazol-1-yl n = 6

$R^1$ = benzoxazol-2-yl

Yellow oil, yield 68%.

NMR (CDCl$_3$).

1.3–1.9 (m, 8H, —(CH$_2$)$_4$—); 2.2 (S, 6H, Me$_3$-, Me$_5$-pyrazole); 3.3 (t, J = 8 Hz, 2H, CH$_2$—S); 3.95 (t, J = 8 Hz, 2H,—CH$_2$—N); 5.75 (S, 1H, H-pyrazole); 7.15–7.75 (m, 4H, H-benzoxazole).

Analysis found: C, 65.83; H, 7.12; N, 12.62; S, 9.61; Required: (C$_{18}$H$_{23}$N$_3$OS); C, 65.62; H, 7.04; N, 12.75; S, 9.73.

EXAMPLE 11

2-[7-(benzoxazol-2-yl) thioheptyl]-4-methylthiazole (11)

R = 4-methylthiazole-2-yl n = 7

$R^1$ = benzoxazol-2-yl

Yellow oil, yield 80%.

NMR (CDCl$_3$).

1.4–1.9 (m, 10H, —(CH$_2$)$_5$—); 2.45 (S, 3H, CH$_3$-thiazole); 3.00 (t, J = 8 Hz, 2H, —CH$_2$-thiazole); 3.3 (t, J = 8 Hz, 2H, —CH$_2$—S); 6.75 (S, 1H, H-thiazole); 7.25–7.65 (m, 4H, H-benzoxazole).

Analysis found: C, 62.57; H, 6.51; N, 7.94; S, 18.32; Required: (C$_{18}$H$_{22}$N$_2$OS$_2$); C, 62.39; H, 6.40; N, 8.08; S, 18.50.

EXAMPLE 12

2-[7-(5-chorobenzimidazol-2-yl) thioheptyl]-4-methyl thiazole (12)

R = 4-methylthiazol-2-yl n = 7

$R^1$ = 5-chlorobenzimidazol-2-yl

Colorless prisms, mp = 110°–112° C., yield 85%.

NMR (CDCl$_3$).

1.3–1.9 (m, 10H, —(CH$_2$)$_5$—), 2.45 (S, 3H, CH$_3$-thiazole); 3.00 (t, J = 8 Hz, 2H, —CH$_2$-thiazole; 3.30 (t, J = 8 Hz, 2H, —CH$_2$—S); 6.75 (S, 1H, H-thiazole); 7.10 (d, J = 2 Hz, H$_7$-benzimidazole); 7.18 (d, J = 2 Hz, 1H, H$_6$-benzimidazole); 7.25 (S, 1H, H$_4$-benzimidazole).

Analysis found: C, 57.12; H, 5.91; N, 10.93; S, 16.76; Required: (C$_{18}$H$_{22}$ClN$_3$S$_2$); C, 56.90; H, 5.84; N, 11.06; S, 16.88.

EXAMPLE 13

2-[6-(5-chlorobenzimidazol-2-yl) thiohexyl]-4-methylthiazole (13)

R = 4-methylthiazol-2-yl n = 6

$R^1$ = 5-chlorobenzimidazol-2-yl

Pale yellow prims, mp = 106°–107° C., yield 64%.

NMR (CDCl$_3$).

1.30–1.8 (m, 8H, —(CH$_2$)$_4$—), 2.45 (S, 3H, CH$_3$-thiazole); 3.00 (t, J = 8 Hz, 2H, —CH$_2$-thiazole; 3.30 (t, J:8 Hz, 2H, —CH$_2$—S); 6.75 (S, 1H, H-thiazole); 7.10 (d, J = 2 Hz, 1H, H$_7$-benzimidazole); 7.18 (d, J = 2 Hz, 1H, H$_6$-benzimidazole); 7.25 (S, 1H, H$_4$-benzimidazole).

Analysis found: C, 55.99; H, 5.58; N, 11.37; S, 17.42; Cl, 9.64; Required: (C$_{17}$H$_{20}$ClN$_3$S$_2$); C, 55.80; H, 5.51; N, 11.48; S, 17.52; Cl, 9.69.

EXAMPLE 14

5-[6-(5-chlorobenzimidazol-2-yl) thiohexyl]-4-methylisothiazole (14)

R = 4-methylisothiazol-5-yl n = 6

$R^1$ = 5-chlorobenzimidazol-2-yl

Colorless prism, mp = 129°–130° C., yield 72%.

NMR (CDCl$_3$).

1.3–1.8 (m, 8H, —(CH$_2$)$_4$—); 2.15 (S, 3H, CH$_3$-isothiazole); 2.80 (t, J = 8 Hz, 2H, —CH$_2$-isothiazole); 3.30 (t, J = 8 Hz, 2H, —CH$_2$—S); 7.10 (d, J = 2 Hz, 1H, H$_7$-benzimidazole); 7.18 (d, J = 2 Hz, 1H, H$_6$-benzimidazole); 7.25 (S, 1H, H$_4$-benzimidazole); 8.15 (S, 1H, H-isothiazole); 9.25 (broad S, 1H, H—N).

Analysis found: C, 56.03; H, 5.60; N, 11.39; S, 17.37; Required: (C$_{17}$H$_{20}$ClN$_3$S$_2$); C, 55.80; H, 5.51; N, 11.48; S, 17.52.

EXAMPLE 15

5-[6-(5-chlorobenzimidazol-2-yl) thiohexyl]isothiazole (15)

R = isothiazol-5-yl n = 6

R¹=5-chlorobenzimidazol-2-yl
Colorless prism, mp=86°-87° C., yield 56%.
NMR (CDCl₃).
1.3-1.8 (m, 8H, —(CH₂)₄—); 2.80 (t, J=8 Hz, 2H, —CH₂-isothiazole); 3.30 (t, J=8 Hz, 2H, —CH₂—S); 6.95 (d, J=2 Hz, 1H, H₄-isothiazole); 7.10 (d, J=2 Hz, 1H, H₇-benzimidazole); 7.18 (d, J=2 Hz, 1H, H₆-benzimidazole); 7.25 (S, 1H, H₄-benzimidazole); 8.35 (d, J=2 Hz, 1H, H₃-isothiazole).

Analysis found: C, 54.83; H, 5.23; N, 11.85; S, 18.11; Required: ($C_{16}H_{18}ClN_3S_2$); C, 54.61; H, 5.16; N, 11.94; S, 18.22.

EXAMPLE 16

1-[6-(1-methylimidazol-2-yl)sulfoxyhexyl]-3,5-dimethylpyrazole (16)

R=3,5-dimethylpyrazol-1-yl
n=6
R¹=methylimidazol-2-yl

1-[6-(1-methylimidazol-2-yl)mercaptohexyl]-3,5-dimethylpyrazole (1.63; 0.0055 mol) was dissolved in 50 ml of dichloromethane and cooled to 0° C. A portion of metachloroperbenzoic acid 80% (1.20 g, 0.0055 mol) was added to the solution while stirring. The mixture was brought to room temperature and stirred for ½ hour, 0.5 g of sodium bisulfite was added to destroy MCPBA excess. The mixture was washed with 5% aqueous solution of sodium bicarbonate (50 ml), and water (50 ml×2). The organic layer was dried over sodium sulfate. Removal of the solvent gave a yellow oil product which was purified by elution from silica gel column using methanol-dichloromethane (5:95) as an eluant to gain 0.93 g light yellow oil. Yield 55%.

NMR (CDCl₃).
1.3-1.8 (m, 8H, —(CH₂)₅—); 2.2 (S, 6H, 2CH₃-pyrazole); 3.45 (t, J=9 Hz, 2H, CH₂—SO), 3.95 (t, J=8 Hz, 2H, CH₂—N); 4.00 (S, 3H, CH₃—N); 5.75 (S, 1H, H-pyrazole); 7.1 (d, J=2 Hz, 1H, H₅-imidazole); 7.2 (d, J=2 Hz, 1H, H₄-imidazole). IR (neat); 1076 cm⁻¹; (S=O).

Analysis found: C, 58.63; H, 7.95; N, 17.98; S, 10.21; Required: ($C_{15}H_{24}N_4OS$); C, 58.41; H, 7.84; N, 18.16; S, 10.39.

Schematic for Preparation of Sulfoxide Compounds

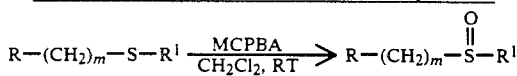

By procedures similar to those used in Example 16, the following compounds were prepared.

EXAMPLE 17

1-[6-(benzoxazol-2-yl)sulfoxyhexyl]-3,5-dimethylpyrazole (17)

R=3,5-dimethylpyrazol-1-yl
n=6
R¹=benzoxazol-2-yl
Yellow oil, yield 40%.

1.3-1.9 (m, 8H, —(CH₂)₄—); 2.2 (S, 6H, Me₃-, Me₅-pyrazole); 3.45 (t, J=9 Hz, 2H, CH₂—S=O); 3.95 (t, J=8 Hz, 2H, —CH₂—N); 5.75 (S, 1H, H-pyrazole); 7.5-8.0 (m, 4H, H-benzoxazole). IR (neat); 1070 cm⁻¹; (S=O).

Analysis found: C, 62.81; H, 6.79; N, 12.07; S, 9.21; Required: ($C_{18}H_{23}N_3O_2S$); C, 62.58; H, 6.71; N, 12.16; S, 9.28.

EXAMPLE 18

1-[6-(5-methylthiodiazol-2-yl)sulfoxyhexyl]-3,5-dimethylpyrazole (18)

R=3,5-dimethylpyrazol-1-yl
n=6
R¹=5-methylthiodizaol-2-yl
Yellow oil, yield 24%.
NMR (CDCl₃).
1.5-1.9 (m, 8H, —(CH₂)₄—); 2.2 (S, 6H, 2 Me, Me₃-, Me₅-pyrazole); 2.9 (S, 3H, CH₃-thiodiazole); 3.45 (t, J=9 Hz, —CH₂—S=O); 3.95 (t, J=8 Hz, —CH₂—N); 5.75 (S, 1H, H-pyrazole). IR (neat); 1076 cm⁻¹; (S=O).

Analysis found: C, 51.72; H, 6.87; N, 17.01; S, 19.43; Required: ($C_{14}H_{22}N_4OS_2$); C, 51.51; H, 6.79; N, 17.16; S, 19.64.

EXAMPLE 19

1-[6-(1-methyltetrazol-5-yl)sulfoxyhexyl]-2,5-dimethylpyrazole (19)

R=3,5-dimethylpyrazol-1-yl
n=6
R¹=1-methyltetrazol-5-yl
Yellow oil, yield 20%.
NMR (CDCl₃).
1.5-1.9 (m, 8H, —(CH₂)₄—); 2.2 (S, 6H, Me₃-, Me₅-pyrazole); 3.45 (t, J=9 Hz, 2H, —CH₂—SO); 3.95 (t, J=8 Hz, 2H, —CH₂—N); 4.35 (s, 3H, CH₃—N of tetrazole); 5.75 (S, 1H, H-pyrazole). IR (neat); 1078 cm⁻¹; (S=O).

Analysis found: C, 50.54; H, 7.25; N, 26.85; S, 10.18; Required: ($C_{13}H_{22}N_6OS$); C, 50.31; H, 7.14; N, 27.06; S, 10.33.

EXAMPLE 20

5-[7-(1-methyltetrazol-5-yl)sulfoxyheptyl]-3-methylisoxazole (20)

R=3-methylisoxazol-5-yl;
n=7
R¹=1-methyltetrazol-5-yl
Yellow oil, yield 40%.
NMR (CDCl₃).
1.5-1.8 (m, 10H, —(CH₂)₅—); 2.3 (S, 3H, CH₃-isoxazole); 2.70 (t, J=8 Hz, 2H, —CH₂-isoxazole); 3.45 (t, J=9 Hz, 2H, —CH₂=SO); 4.35 (S, 3H, CH₃—N of tetrazole); 5.8 (S, 1H, H-isoxazole). IR (neat); 1076 cm⁻¹; (S=O)

Analysis found: C, 50.33; H, 6.91; N, 22.35; S, 10.18; Required: ($C_{13}H_{21}N_5O_2S$); C, 50.14; H, 6.80; N, 22.49; S, 10.30.

EXAMPLE 21

5-[7-(5-methylthiodiazol-2-yl)sulfoxyheptyl]-3-methylisoxazole (21)

R=3-methylisoxazol-5-yl
n=7
R¹=5-methylthiodiazol-2-yl
Colorless prism, mp=80°-82° C.; yield 40%.
NMR (CDCl₃).
1.5-1.8 (m, 10H, —(CH₂)₅—); 2.3 (S, 3H, CH₃-isoxazole); 2.70 (t, J=8 Hz, 2H, —CH₂-isoxazole); 2.9 (S, 3H, CH₃-thiodiazole); 3.45 (t, J=9 Hz, 2H, —CH₂—SO); 5.8 (S, 1H, H-isoxazole). IR (neat); 1078 cm⁻¹; (S=O).

Analysis found: C, 51.52; H, 6.54; N, 12.68; S, 19.43;
Required: ($C_{14}H_{21}N_3O_2S_2$); C, 51.35; H, 6.46; N, 12.83; S, 19.58.

EXAMPLE 22

5-[7-(1-methylimidazol-2-yl)sulfoxyheptyl]-3-methylisoxazole (22)

R = 3-methylisoxazol-5-yl
n = 7
$R^1$ = 1-methylimidazol-2-yl
Yellow oil, yield 40%.
NMR ($CDCl_3$).

1.5-1.8 (m, 10H, —$(CH_2)_5$—); 2.3 (S, 3H, $CH_3$-isoxazole); 2.70 (t, J=8 Hz, 2H, —$CH_2$-isoxazole); 3.45 (t, J=9 Hz, 2H, —$CH_2$—SO); 4.00 (S, 3H, $CH_3$—N); 5.8 (S, 1H, H-isoxazole); 7.05 (d, J=2 Hz, 1H, $H_5$-imidazole); 7.15 (d, J=2 Hz, 1H, $H_4$-imidazole). IR (neat); 1078 cm$^{-1}$; (S=O).

Analysis found: C, 58.44; H, 7.56; N, 13.45; S, 10.24;
Required: ($C_{15}H_{23}N_3O_2S$); C, 58.23; H, 7.49; N, 13.58; S, 10.36.

EXAMPLE 23

5-[7-(benzimidazol-2-yl)sulfoxyheptyl]-3-methylisoxazole (23)

R = 3-methylisoxazol-5-yl
n = 7
$R^1$ = benzimidazol-2-yl
Colorless prism, mp=56°-58° C., yield 23%.
NMR ($CDCl_3$).

1.3-1.9 (m, 10H, —$(CH_2)_5$—); 2.3 (S, 1H, H-isoxazole); 2.70 (t, J=8 Hz, 2H, —$CH_2$-isoxazole); 3.45 (t, J=9 Hz, 2H, —$CH_2$—SO); 5.8 (S, 1H, H-isoxazole); 7.3-7.5 (m, 4H, H-benzimidazole); 7.75 (broad S, 1H, H—N). IR (neat); 1076 cm$^{-1}$; (S=O).

Analysis found: C, 62.79; H, 6.79; N, 12.01; S, 9.15;
Required: ($C_{18}H_{23}N_3O_2S$); C, 62.58; H, 6.71; N, 12.16; S, 9.28.

EXAMPLE 24

2-[7-(benzoxazol-2-yl)sulfoxyheptyl]-4-methylthiazole (24)

R = 4-methylthiazol-2-yl
n = 7
$R^1$ = benzoxazol-2-yl
Yellow oil, yield 63%.
NMR ($CDCl_3$).

1.4-1.9 (m, 10H, —$(CH_2)_5$—); 2.45 (S, 3H, $CH_3$-thiazole); 3.00 (t, J=8 Hz, 2H, —$CH_2$-thiazole); 3.45 (t, J=9 Hz, 2H, —$CH_2$—SO); 6.75 (S, 1H, H-thiazole); 7.45-7.9 (m, 4H, H-benzoxazole). IR (neat); 1065 cm$^{-1}$; (S=O).

Analysis found: C, 59.86; H, 6.21; N, 7.47; S, 17.48;
Required: ($C_{18}H_{22}N_2O_2S_2$); C, 59.64; H, 6.12; N, 7.73; S, 17.69.

EXAMPLE 25

5-[7-(1-methyltetrazol-5-yl)sulfoxyheptyl]-3-methylisoxazole (25)

R = 3-methylisoxazol-5-yl
n = 7
$R^1$ = methyltetrazol-5-yl

A mixture of 5-[7-(1-methyltetrazol-5-yl)mercaptoheptyl]-3-methylisoxazole (0.59 g, 0.002 mol) and metachloroperbenzoic acid 84% (0.817 g, 0.004 mol) in dichloromethane (40 ml) was stirred at room temperature for 3 hours. The mixture was washed with a solution of sodium hydroxide 2N (20 ml) and water (50 ml×2). The organic layer was dried over sodium sulfate and evaporated to remove all the solvent to give a yellow solid product. The solid product was treated with hexane: ethyl acetate (4:1) (20 ml) and filtered. The remaining solid was recrystallized in hot ether to provide colourless prisms (350 mg). (yield 53%) mp=58°-60° C.
NMR ($CDCl_3$).

1.3-1.9 (m, 10H, —$(CH_2)_5$—); 2.3 (S, 1H, H-isoxazole); 2.70 (t, J=8 Hz, 2H, —$CH_2$-isoxazole); 3.45 (t, J=9 Hz, 2H, $CH_2$—$SO_2$); 4.3 (S, 3H, $CH_3$—N); 5.8 (S, 1H, 1H, H-isoxazole). IR (neat); 1145 cm$^{-1}$; (O=S=O)

Analysis found: C, 47.91; H, 6.58; N, 21.23; S, 9.68;
Required: ($C_{13}H_{21}N_5O_3S$); C, 47.69; H, 6.47; N, 21.39; S, 9.79.

EXAMPLE 26

2-[7-(benzoxazol-2-yl)sulfoxyheptyl]-4-methylthiazole (26)

R = 4-methylthiazol-2-yl
n = 7
$R^1$ = benzoxazol-2-yl

2-[(benzoxazol-2-yl)mercaptoheptyl]-4-methylthiazole (1.362 g, 0.0039 mol) was dissolved in 25 ml of glacial acetic acid. After the addition of 5 ml of water, potassium permanganate (1.24 g, 0.0078 mol) was added to the solution while stirring at room temperature. The mixture was stirred for 30 minutes, the color of the solution changed from dark purple to brown, at which time 10 ml of hydrogen peroxide (30%) was added to decolorize the solution. 10 ml of ice+water was added to the mixture. The water and acetic acid were removed by evaporation under reduced pressure in a water bath. 1.5 g dark yellow oil, which was purified by elution from silica gel column using hexanes ethyl acetate (3:2) provided 0.586 g of a light yellow oil. yield 42%.

NMR 1.4-1.9 (m, 10H, —$(CH_2)_5$—); 2.45 (S, 3H, $CH_3$-thiazole); 3.00 (t, J=8 Hz, 2H, —$CH_2$-thiazole); 3.45 (t, J=9 Hz, 2H, —$CH_2$—$SO_2$); 6.75 (S, 1H, H-thiazole); 7.50-8.05 (m, 4H, H-benzoxazole). IR (neat) 1162 cm$^{-1}$; (O=S=O).

Analysis found: C, 57.41; H, 5.94; N, 7.26; S, 16.72;
Required: ($C_{18}H_{22}N_2O_3S_2$); C, 57.12; H, 5.86; N, 7.40; S, 16.94.

Schematic for Preparation of Sulfone Compounds

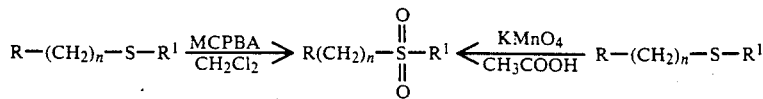

By the procedures similar to those used in example 25 and 26, the following compounds were prepared.

EXAMPLE 27

5-[7-(5-methylthiodiazol-2-yl)sulfonylheptyl]-3-methylisoxazole (27)

R = 3-methylisoxazol-5-yl
n = 7
$R^1$ = 5-methylthiodiazol-2-yl

Colorless prism, mp = 80°–81° C., yield 45%.
NMR (CDCl$_3$).
1.3–1.9 (m, 10H, —(CH$_2$)$_5$—); 2.3 (S, 1H, H-isoxazole); 2.70 (t, J = 8 Hz, 2H, CH$_2$-isoxazole); 2.9 (S, 3H, CH$_3$-thiodiazole); 3.45 (t, J = 9 Hz, 2H, —CH$_2$—SO$_2$); 5.8 (S, 1H, H-isoxazole). IR (neat); 1156 cm$^{-1}$; O=S=O.

Analysis found: C, 49.19; H, 6.25; N, 12.11; S, 18.51; Required: (C$_{14}$H$_{21}$N$_3$O$_3$S$_2$); C, 48.96; H, 6.16; N, 12.23; S, 18.67.

EXAMPLE 28

1-[6-(5-methylthiodiazol-2-yl)sulfonylhexyl]-3,5-dimethylpyrazole (28)

R = 3,5-dimethylpyrazol-1-yl
n = 6
$R^1$ = 5-methylthiodiazol-2-yl

Colorless prism, mp = 50°–51° C., yield 23%.
NMR (CDCl$_3$).
1.3–1.8 (m, 8H, —(CH$_2$)$_4$—); 2.2 (S, 6H, Me$_3$- Me$_5$-pyrazole); 2.9 (S, 3H, CH$_3$-thiodiazole); 3.45 (T, J = 9 Hz, 2H, CH$_2$—SO$_2$); 3.95 (t, J = 8 Hz, 2H, —CH$_2$—N); 5.75 (S, 1H, H-pyrazole). IR (neat); 1160 cm$^{-1}$; (O=S=O).

Analysis found: C, 49.33; H, 6.55; N, 16.19; S, 18.57; Required: (C$_{14}$H$_{22}$N$_4$O$_2$S$_2$); C, 49.10; H, 6.47; N, 16.36; S, 18.72.

EXAMPLE 29

1-[6-(1-methyltetrazol-5-yl)sulfonylhexyl]-3,5-dimethylpyrazole (29)

R = 3,5-dimethylpyrazol-1-yl
n = 6
$R^1$ = 1-methyltetrazol-5-yl

Yellow oil, yield 20%.
NMR (CDCl$_3$).
1.3–1.9 (m, 8H, —(CH$_2$)$_4$—); 2.2 (S, 6H, Me$_3$-, Me$_5$-pyrazole); 3.45 (t, J = 9 Hz, 2H, CH$_2$—SO$_2$); 3.95 (t, J = 8 Hz, 2H, CH$_2$—N); 4.3 (S, 3H, CH$_3$—N); 5.75 (S, 1H, H-pyrazole). IR (neat); 1168 cm$^{-1}$; (O=S=O).

Analysis found: C, 48.06; H, 6.87; N, 25.55; S, 9.71; Required: (C$_{13}$H$_{22}$N$_6$O$_2$S); C, 47.84; H, 6.79; N, 25.74; S, 9.82.

EXAMPLE 30

5-[7-(1-methylimidazol-2-yl)sulfonylheptyl]-3-methylisoxazole (30)

R = 3-methylisoxazol-5-yl
n = 7
$R^1$ = methylimidazol-2-yl

Colorless prisms, mp = 54°–55° C.; yield 41%.
NMR (CDCl$_3$).
1.5–1.8 (m, 10H, —(CH$_2$)$_5$—); 2.3 (S, 3H, CH$_3$-isoxazole); 2.70 (t, J = 8 Hz, 2H, —CH$_2$—SO$_2$); 4.00 (S, 3H, CH$_3$—N); 5.8 (S, 1H, H-isoxazole); 7.00 (d, J = 2 Hz, 1H, H$_5$-imidazole); 7.10 (d, J = 2 Hz, 1H, H$_4$-imidazole). IR (neat); 1160 cm$^{-1}$; (O=S=O).

Analysis found: C, 55.57; H, 7.21; N, 12.99; S, 9.61; Required: (C$_{15}$H$_{23}$N$_3$O$_3$S); C, 55.36; H, 7.12; N, 12.91; S, 9.85.

ANTI-RHINOVIRUS ACTIVITY EXPERIMENTS

The experiments were performed by a cytopathic effect inhibition method and a neutral red dye uptake assay adapted from the method for activity against Herpes Simplex virus developed by M. Nixon Ellis, Ch. 18 Clinical Virology Manual—Specter, S. Lancz, G. (1986).

Materials:

WI38 cells (source ATCC)
Rhinovirus Types: 1A, 1B, 2, 4, 15, 17, 23, 29, 30, 31, 32, 36, 39, 44, 49, 53, 56, 63, 86, 88 (source ATCC)
Minimum Essential Medium, Eagle (Modified with Earles salt) supplemented with 10% Fetal bovine serum, 100 iuml$^{-1}$ penicillin G, 100 μgml$^{-1}$ streptomycin and Non-Essential Aminoacids (Sigma M2025)
Drugs dissolved in DMSO to 20 mg ml$^{-1}$ and further diluted in the 10% FBS-MEM
P.B.S. at pH 6.0
Citrate/Methanol buffer (0.1M citric acid, 157.5 ml; 0.1M Sodium Citrate, 92.5 ml; dionised H$_2$O 250 ml; methanol, 500 ml)
Neutral red dye.

Procedure

50 μl of each concentration of drug was added (in duplicate) to wells of a 96 well plate. Three wells per plate had medium instead of drug as cell or virus control. The wells were seeded with 100 μl of WI38 cells at $8.0 \times 10^5$ cells ml$^{-1}$. 50 μl of virus was added to each well at a dilution (usually 10 TCID$_{50}$) which would give 100% cytopathic effect after 3 days. A control plate was always set up in parallel which had no virus added. The plates were incubated at 33° C. in a 95% air/5% CO$_2$, humidified atmosphere for 3–4 days. When 100% c.p.e. had developed (3–4 days) the cpe/toxic effect was first scored visually using an inverted microscope. The drug concentration at which virus growth was inhibited by 50% was called the minimum inhibitory concentration (MIC$_{50}$). The toxic concentration was calculated by noting the concentration at which there was a change in morphology in 25% of the cells compared to cell controls.

The plates were then subjected to the dye uptake assay. The plates were washed with phosphate buffered saline (P.B.S.) at pH 6.0. Then 250 μl of 0.025% Neutral red/PBS pH 6.0 was added per well and incubated for 45 minutes at 37° C.

The plates were then washed again with PBS pH 6.0 and 250 μl of citrate-methanol buffer was added per well and incubated for 60 minutes at 37° C. The plates were then read on a multiscan spectrophotometer with a 540 mm filter. The cell control was denoted 100% and relative to this the concentration of drug inhibiting virus growth by 50% was termed MIC$_{50}$. If the concentration of the drug inhibited cell growth by 25% this was referred to as toxic.

It will be noted that the results obtained by the cytopathic effect inhibition method and the dye uptake method were usually identical, if not the higher value was quoted.

The selected compounds of this invention were tested against HRV-1A and HRV-39. The results are shown in Table I given herebelow.

TABLE I

Toxicity and Activity (MIC-50) of Some Compounds ($\mu gml^{-1}$)

| Compound No. | Toxicity | Rhinovirus-1A | Rhinovirus-39 |
|---|---|---|---|
| WIN-51711 (Disoxaril) | 50 | 10 | 25 |
| 3 | 50 | 25 | 25 |
| 4 | 25 | 10 | 5 |
| 6 | 50 | NA | 10 |
| 10 | 50 | NA | 10 |
| 11 | 50 | 25 | 10 |
| 13 | 50 | 10 | 10 |
| 23 | 50 | 25 | 10 |
| 30 | 50 | 50 | NA |

MIC = Minimum Inhibitory Concentration
NA = Not Active

Compounds 4 and 13 which showed activity comparable to Disoxaril have been tested against twenty serotypes of Rhinoviruses (HRV's 1A, 1B, 2, 4, 15, 17, 23, 29, 30, 31, 32, 36, 39, 44, 49, 53, 56, 63, 86, 88) to evaluate the range of activity in comparison therewith. The results are summarized in Table II, given below.

TABLE II

Toxicity and Activity (MIC50) of Some Compounds ($\mu gml^{-1}$)

| Compound No. | 4 | 13 | Disoxaril WIN-51711 |
|---|---|---|---|
| Toxicity | 25 | 50 | 50 |
| Rhinovirus type | | | |
| 1A | 10 | 10 | 25 |
| 1B | NA | 10 | 25 |
| 2 | 10 | NA | NA |
| 4 | NA | 5 | 0.5 |
| 15 | 5 | 5 | 5 |
| 17 | 5 | 5 | <0.5 |
| 23 | 5 | 5 | 10 |

2-[6-(5-chlorobenzimidazol-2-yl)thiohexyl]-4-methylthiazole (13) showed strog activity against coxsacki virus type 1B (MIC50=1 $\mu gml^{-1}$. In comparison Disoxaril ™ had an MIC50 of 10 $\mu gml^{-1}$.

In summary, the compounds of this invention can be utilized in the prevention or treatment of common cold, aspectic meningitis, myocarditis, and meningoencephalitis caused by rhinoviruses and coxsacki virus type B1.

The embodiments of the invention in which an exclusive property or privilege is claimed are defined as follows:

1. Compounds having the formulae

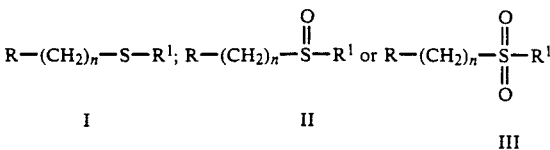

wherein

R is 3-methylisoxazol-5-yl;

n is 5, 6, 7 or 8; and $R^1$ is a substituted, fused or non-fused azole moiety.

2. A compound according to claim 1, wherein $R^1$ is a nonfused azole.

3. A compound according to claim 2, wherein $R^1$ is 1-methyltetrazol-3-yl.

4. 5-[7-(1-methyltetrazol-5-yl)thioheptyl]-3-methylisoxazole according to claim 1.

5. 5-[7-(5-methylthiodiazole-2-yl)thioheptyl]-3-methylisoxazole according to claim 1.

6. 5-[7-(1-methylimidazol-2-yl)thioheptyl]-3-methylisoxazole according to claim 1.

7. 5-[7-(benzimidazol-2-yl)thioheptyl]-3-methylisoxazole according to claim 1.

8. 5-[7-(5-chlorobenzimidazol-2-yl)thioheptyl]-3-methylisoxazole according to claim 1.

9. 5-[7-(benzothiazol-2-yl)thioheptyl]-3-methylisoxazole according to claim 1.

10. 5-[7-(1-methyltetrazol-5-yl)sulfoxyheptyl]-3-methylisoxazole according to claim 1.

11. 5-[7-(5-methylthiodiazol-2-yl)sulfoxyheptyl]-3-methylisoxazole according to claim 1.

12. 5-[7-(methylimidazol-2-yl)sulfoxyheptyl]-3-methylisoxazole according to claim 1.

13. 5-[7-(benzimidazol-2-yl)sulfoxyheptyl]-3-methylisoxazole according to claim 1.

14. 5-[7-(1-methyltetrazol-5-yl)sulfonylheptyl]-3-methylisoxazole according to claim 1.

15. 5-[7-(5-methylthiodiazol-2-yl)sulfonylheptyl]-3-methylisoxazole according to claim 1.

16. 5-[7-(1-methylimidazol-2-yl)sulfonylheptyl]-3-methylisoxazole according to claim 1.

* * * * *